(12) United States Patent
Palm et al.

(10) Patent No.: US 8,038,718 B2
(45) Date of Patent: Oct. 18, 2011

(54) MULTI-COMPOSITE DISC PROSTHESIS

(75) Inventors: Eric E. Palm, St. Louis Park, MN (US);
Jeffrey C. Felt, Excelsior, MN (US);
Jenny Zeroni, St. Louis Park, MN (US);
Albert Schafer, Elk River, MN (US)

(73) Assignee: Vertebral Technologies, Inc., Minnetonka, MN (US)

( * ) Notice: Subject to any disclaimer, the term of this patent is extended or adjusted under 35 U.S.C. 154(b) by 113 days.

(21) Appl. No.: 11/489,264

(22) Filed: Jul. 19, 2006

(65) Prior Publication Data
US 2007/0027546 A1 Feb. 1, 2007

Related U.S. Application Data

(60) Provisional application No. 60/700,459, filed on Jul. 19, 2005.

(51) Int. Cl.
*A61F 2/44* (2006.01)
(52) U.S. Cl. .................................. 623/17.16
(58) Field of Classification Search .... 623/17.11–17.16; 606/246, 248, 279, 86 A, 99
See application file for complete search history.

(56) References Cited

U.S. PATENT DOCUMENTS

| | | | |
|---|---|---|---|
| 3,030,951 A | 4/1962 | Mandarino | |
| 3,728,742 A | 4/1973 | Averill et al. | |
| 3,815,599 A | 6/1974 | Deyerle | |
| 3,848,601 A | 11/1974 | Ma et al. | |
| 3,867,728 A | 2/1975 | Stubstad et al. | |
| 3,867,729 A | 2/1975 | Stubstad et al. | |
| 4,081,866 A | 4/1978 | Upshaw et al. | |
| 4,203,444 A | 5/1980 | Bonnell et al. | |
| 4,349,921 A | 9/1982 | Kuntz | |
| 4,456,745 A | 6/1984 | Rajan | |
| 4,463,141 A | 7/1984 | Robinson | |
| 4,476,293 A | 10/1984 | Robinson | |
| 4,477,604 A | 10/1984 | Oechsle, III | |
| 4,502,161 A | 3/1985 | Wall | |
| 4,647,643 A | 3/1987 | Zdrahala et al. | |
| 4,651,736 A | 3/1987 | Sanders | |

(Continued)

FOREIGN PATENT DOCUMENTS
DE 43 39 895 3/1995
(Continued)

OTHER PUBLICATIONS

U.S. Appl. No. 11/372,447, filed Mar. 1, 2007, Felt et al.

(Continued)

*Primary Examiner* — Thomas C Barrett
*Assistant Examiner* — Sameh Boles
(74) *Attorney, Agent, or Firm* — Patterson Thuente Christensen Pedersen, PA

(57) ABSTRACT

A multi-composite disc prosthesis is adapted to be implanted within the annulus of an evacuated disc nucleus space in a human spine. The disc prosthesis has a generally solid unitary body with a size and a shape adapted to be positioned within the annulus of the evacuated disc nucleus space. The body has an outer portion comprised of a first biomaterial and an inner portion comprised of a second biomaterial. The second biomaterial has a compressive modulus that is harder than a compressive modulus of the first biomaterial and the first and second biomaterials are chemically or physically bonded to form a multi-composite material that forms the solid body.

29 Claims, 3 Drawing Sheets

U.S. PATENT DOCUMENTS

| | | | |
|---|---|---|---|
| 4,711,639 A | 12/1987 | Grundei | |
| 4,722,948 A | 2/1988 | Sanderson | |
| 4,743,256 A | 5/1988 | Brantigan | |
| 4,743,632 A | 5/1988 | Marinovic | |
| 4,772,287 A | 9/1988 | Ray et al. | |
| 4,808,691 A | 2/1989 | Konig et al. | |
| 4,834,757 A | 5/1989 | Brantigan | |
| 4,863,476 A | 9/1989 | Shepperd | |
| 4,873,308 A | 10/1989 | Coury et al. | |
| 4,880,610 A | 11/1989 | Constantz | |
| 4,904,260 A | 2/1990 | Ray et al. | |
| 4,911,718 A * | 3/1990 | Lee et al. | 623/17.15 |
| 4,969,888 A | 11/1990 | Scholten et al. | |
| 5,007,940 A | 4/1991 | Berg | |
| 5,047,055 A | 9/1991 | Bao et al. | |
| 5,067,964 A | 11/1991 | Richmond et al. | |
| 5,082,803 A | 1/1992 | Sumita | |
| 5,108,404 A | 4/1992 | Scholten et al. | |
| 5,109,077 A | 4/1992 | Wick | |
| 5,143,942 A | 9/1992 | Brown | |
| 5,166,115 A | 11/1992 | Brown | |
| 5,192,326 A | 3/1993 | Bao et al. | |
| 5,192,327 A | 3/1993 | Brantigan | |
| 5,254,662 A | 10/1993 | Szycher et al. | |
| 5,263,987 A | 11/1993 | Shah | |
| 5,278,201 A | 1/1994 | Dunn et al. | |
| 5,344,458 A | 9/1994 | Bonutti | |
| 5,344,459 A | 9/1994 | Swartz | |
| 5,397,364 A | 3/1995 | Kozak et al. | |
| 5,458,643 A | 10/1995 | Oka et al. | |
| 5,509,934 A | 4/1996 | Cohen | |
| 5,514,180 A | 5/1996 | Heggeness | |
| 5,522,899 A | 6/1996 | Michelson | |
| 5,525,418 A | 6/1996 | Hashimoto et al. | |
| 5,545,229 A | 8/1996 | Parsons et al. | |
| 5,549,683 A | 8/1996 | Bonutti | |
| 5,554,191 A | 9/1996 | Lahille et al. | |
| 5,556,429 A | 9/1996 | Felt | |
| 5,562,736 A | 10/1996 | Ray et al. | |
| 5,609,635 A | 3/1997 | Michelson | |
| 5,624,463 A | 4/1997 | Stone et al. | |
| 5,674,294 A | 10/1997 | Bainville et al. | |
| 5,702,453 A | 12/1997 | Rabbe et al. | |
| 5,702,454 A | 12/1997 | Baumgartner | |
| 5,725,531 A | 3/1998 | Shapiro | |
| 5,755,797 A | 5/1998 | Baumgartner | |
| 5,772,661 A | 6/1998 | Michelson | |
| 5,776,199 A | 7/1998 | Michelson | |
| 5,795,353 A | 8/1998 | Felt | |
| 5,800,547 A | 9/1998 | Schafer et al. | |
| 5,824,093 A | 10/1998 | Ray et al. | |
| 5,860,973 A | 1/1999 | Michelson | |
| 5,861,041 A | 1/1999 | Tienboon et al. | |
| 5,888,220 A | 3/1999 | Felt et al. | |
| 5,888,227 A | 3/1999 | Cottle | |
| 5,888,228 A | 3/1999 | Knothe et al. | |
| 5,893,889 A | 4/1999 | Harringson | |
| 5,919,236 A | 7/1999 | Pfaff et al. | |
| 5,944,759 A | 8/1999 | Link | |
| 5,980,522 A | 11/1999 | Koros et al. | |
| 5,989,289 A | 11/1999 | Coates et al. | |
| 5,989,291 A | 11/1999 | Ralph et al. | |
| 6,033,438 A | 3/2000 | Bianchi et al. | |
| 6,048,345 A | 4/2000 | Berke et al. | |
| 6,079,868 A | 6/2000 | Rydell | |
| 6,080,193 A | 6/2000 | Hochshuler et al. | |
| 6,096,038 A | 8/2000 | Michelson | |
| 6,096,080 A | 8/2000 | Nicholson et al. | |
| 6,102,950 A | 8/2000 | Vaccaro | |
| 6,110,210 A | 8/2000 | Norton et al. | |
| 6,113,638 A | 9/2000 | Williams et al. | |
| 6,117,174 A | 9/2000 | Nolan | |
| 6,132,472 A | 10/2000 | Bonutti | |
| 6,139,579 A | 10/2000 | Steffee et al. | |
| 6,140,452 A | 10/2000 | Felt et al. | |
| 6,143,033 A | 11/2000 | Paul et al. | |
| 6,146,422 A | 11/2000 | Lawson | |
| 6,159,211 A | 12/2000 | Boriani et al. | |
| 6,174,311 B1 | 1/2001 | Branch et al. | |
| 6,176,882 B1 | 1/2001 | Bledermann et al. | |
| 6,183,517 B1 | 2/2001 | Suddaby | |
| 6,190,414 B1 | 2/2001 | Young et al. | |
| 6,206,923 B1 | 3/2001 | Boyd et al. | |
| 6,206,927 B1 | 3/2001 | Fell et al. | |
| 6,224,630 B1 | 5/2001 | Bao et al. | |
| 6,224,631 B1 | 5/2001 | Kohrs | |
| 6,245,108 B1 | 6/2001 | Biscup | |
| 6,248,131 B1 | 6/2001 | Felt et al. | |
| 6,251,140 B1 | 6/2001 | Marino et al. | |
| 6,258,125 B1 | 7/2001 | Paul et al. | |
| 6,264,695 B1 | 7/2001 | Stoy | |
| 6,270,528 B1 | 8/2001 | McKay | |
| 6,302,914 B1 | 10/2001 | Michelson | |
| 6,342,075 B1 | 1/2002 | MacArthur | |
| 6,348,071 B1 | 2/2002 | Steffee et al. | |
| 6,371,990 B1 | 4/2002 | Ferree | |
| 6,387,130 B1 | 5/2002 | Stone et al. | |
| 6,419,704 B1 | 7/2002 | Ferree | |
| 6,419,705 B1 | 7/2002 | Erickson | |
| 6,436,140 B1 | 8/2002 | Liu et al. | |
| 6,436,143 B1 | 8/2002 | Ross et al. | |
| 6,440,169 B1 | 8/2002 | Elberg et al. | |
| 6,443,988 B2 | 9/2002 | Felt et al. | |
| 6,468,311 B2 * | 10/2002 | Boyd et al. | 623/17.16 |
| 6,488,710 B2 | 12/2002 | Besselink | |
| 6,511,509 B1 | 1/2003 | Ford et al. | |
| 6,524,341 B2 | 2/2003 | Lang et al. | |
| 6,533,818 B1 | 3/2003 | Weber et al. | |
| 6,537,280 B2 | 3/2003 | Dinger et al. | |
| 6,558,421 B1 | 5/2003 | Fell et al. | |
| 6,558,424 B2 | 5/2003 | Thalgott | |
| 6,562,074 B2 | 5/2003 | Gerbec et al. | |
| 6,595,998 B2 | 7/2003 | Johnson et al. | |
| 6,610,092 B2 | 8/2003 | Ralph et al. | |
| 6,610,093 B1 | 8/2003 | Pisharodi | |
| 6,620,196 B1 | 9/2003 | Trieu | |
| 6,648,917 B2 | 11/2003 | Gerbec et al. | |
| 6,652,587 B2 | 11/2003 | Felt et al. | |
| 6,669,732 B2 | 12/2003 | Serhan et al. | |
| 6,726,720 B2 | 4/2004 | Ross et al. | |
| 6,726,721 B2 | 4/2004 | Stoy et al. | |
| 6,733,535 B2 | 5/2004 | Michelson | |
| 6,740,093 B2 | 5/2004 | Hochschuler et al. | |
| 6,764,514 B1 | 7/2004 | Li et al. | |
| 6,770,095 B2 | 8/2004 | Grinberg et al. | |
| 6,773,460 B2 | 8/2004 | Jackson | |
| 6,793,678 B2 | 9/2004 | Hawkins | |
| 6,821,298 B1 | 11/2004 | Jackson | |
| 6,835,206 B2 | 12/2004 | Jackson | |
| 6,852,129 B2 | 2/2005 | Gerbec et al. | |
| 6,855,165 B2 | 2/2005 | Fell et al. | |
| 6,855,167 B2 | 2/2005 | Shimp et al. | |
| 6,866,684 B2 | 3/2005 | Fell et al. | |
| 6,893,463 B2 | 5/2005 | Fell et al. | |
| 6,896,701 B2 | 5/2005 | Boyd et al. | |
| 6,911,044 B2 | 6/2005 | Fell et al. | |
| 6,923,831 B2 | 8/2005 | Fell et al. | |
| 6,966,928 B2 | 11/2005 | Fell et al. | |
| 7,001,431 B2 * | 2/2006 | Bao et al. | 623/17.12 |
| 7,008,452 B2 | 3/2006 | Hawkins | |
| 7,018,416 B2 | 3/2006 | Hanson et al. | |
| 7,238,204 B2 | 7/2007 | Le Couedic et al. | |
| 7,267,690 B2 | 9/2007 | Felt | |
| 7,291,171 B2 | 11/2007 | Ferree | |
| 7,297,161 B2 | 11/2007 | Fell | |
| 7,320,709 B2 | 1/2008 | Felt et al. | |
| 7,341,602 B2 | 3/2008 | Fell et al. | |
| 7,491,235 B2 | 2/2009 | Fell | |
| 7,491,237 B2 | 2/2009 | Randall et al. | |
| 7,563,285 B2 | 7/2009 | Ralph et al. | |
| 7,591,853 B2 | 9/2009 | Felt et al. | |
| 7,621,960 B2 | 11/2009 | Boyd et al. | |
| 7,666,228 B2 | 2/2010 | Le Couedic et al. | |
| 7,914,582 B2 | 3/2011 | Felt et al. | |
| 2001/0004710 A1 * | 6/2001 | Felt et al. | 623/17.12 |
| 2002/0026244 A1 | 2/2002 | Trieu | |
| 2002/0029084 A1 | 3/2002 | Paul et al. | |

| | | |
|---|---|---|
| 2002/0099444 A1 | 7/2002 | Boyd et al. |
| 2002/0127264 A1 | 9/2002 | Felt et al. |
| 2002/0128713 A1 | 9/2002 | Ferree |
| 2002/0183850 A1 | 12/2002 | Felt et al. |
| 2003/0055506 A1 | 3/2003 | Stoy et al. |
| 2003/0065396 A1 | 4/2003 | Michelson |
| 2003/0130739 A1 | 7/2003 | Gerbec et al. |
| 2003/0135279 A1 | 7/2003 | Michelson |
| 2003/0220691 A1* | 11/2003 | Songer et al. ............... 623/17.14 |
| 2003/0230198 A1 | 12/2003 | Zittel |
| 2003/0236571 A1 | 12/2003 | James et al. |
| 2004/0002761 A1 | 1/2004 | Rogers et al. |
| 2004/0006393 A1 | 1/2004 | Burkinshaw |
| 2004/0010318 A1 | 1/2004 | Ferree |
| 2004/0019354 A1 | 1/2004 | Johnson et al. |
| 2004/0054413 A1 | 3/2004 | Higham et al. |
| 2004/0059421 A1 | 3/2004 | Glenn et al. |
| 2004/0064144 A1 | 4/2004 | Johnson et al. |
| 2004/0111155 A1 | 6/2004 | Ferree |
| 2004/0127994 A1 | 7/2004 | Kast et al. |
| 2004/0162618 A1 | 8/2004 | Mujwid et al. |
| 2004/0172134 A1 | 9/2004 | Berry |
| 2004/0186576 A1 | 9/2004 | Biscup et al. |
| 2004/0220580 A1 | 11/2004 | Johnson et al. |
| 2004/0220672 A1 | 11/2004 | Shadduck |
| 2004/0225363 A1 | 11/2004 | Richelsoph |
| 2004/0230198 A1 | 11/2004 | Manzi et al. |
| 2004/0267366 A1 | 12/2004 | Kruger |
| 2004/0267367 A1 | 12/2004 | O'Neill |
| 2005/0010290 A1 | 1/2005 | Hawkins |
| 2005/0010295 A1 | 1/2005 | Michelson |
| 2005/0015150 A1 | 1/2005 | Lee |
| 2005/0033424 A1 | 2/2005 | Fell |
| 2005/0055097 A1 | 3/2005 | Grunberg et al. |
| 2005/0131543 A1 | 6/2005 | Benzel et al. |
| 2005/0154463 A1* | 7/2005 | Trieu ........................ 623/17.16 |
| 2005/0154465 A1 | 7/2005 | Hodges et al. |
| 2005/0187633 A1 | 8/2005 | Ferree |
| 2005/0203599 A1 | 9/2005 | Garabedian et al. |
| 2005/0234555 A1 | 10/2005 | Sutton et al. |
| 2005/0240267 A1 | 10/2005 | Randall et al. |
| 2005/0273178 A1 | 12/2005 | Boyan et al. |
| 2006/0004454 A1 | 1/2006 | Ferree et al. |
| 2006/0058807 A1 | 3/2006 | Landry et al. |
| 2006/0058880 A1 | 3/2006 | Wysocki et al. |
| 2006/0069438 A1 | 3/2006 | Zucherman et al. |
| 2006/0106462 A1 | 5/2006 | Tsou |
| 2006/0142858 A1 | 6/2006 | Colleran et al. |
| 2006/0142862 A1 | 6/2006 | Diaz et al. |
| 2006/0149383 A1 | 7/2006 | Arnin et al. |
| 2006/0167550 A1 | 7/2006 | Snell et al. |
| 2006/0173542 A1 | 8/2006 | Shikinami |
| 2006/0178745 A1 | 8/2006 | Bartish et al. |
| 2006/0189999 A1 | 8/2006 | Zwirkoski |
| 2006/0195191 A1 | 8/2006 | Sweeney et al. |
| 2006/0212118 A1 | 9/2006 | Abernathie |
| 2006/0235535 A1 | 10/2006 | Ferree et al. |
| 2006/0247778 A1* | 11/2006 | Ferree et al. ............... 623/17.14 |
| 2006/0259144 A1 | 11/2006 | Trieu |
| 2006/0264965 A1 | 11/2006 | Shadduck et al. |
| 2006/0293756 A1 | 12/2006 | Felt |
| 2007/0027546 A1 | 2/2007 | Palm |
| 2007/0032874 A1 | 2/2007 | Lee et al. |
| 2007/0050036 A1 | 3/2007 | Felt |
| 2007/0233255 A1 | 10/2007 | Song et al. |
| 2007/0244485 A1 | 10/2007 | Greenhalgh et al. |
| 2008/0065220 A1 | 3/2008 | Alleyne et al. |
| 2008/0119853 A1 | 5/2008 | Felt |
| 2008/0133017 A1 | 6/2008 | Beyar et al. |
| 2008/0140206 A1 | 6/2008 | Felt |
| 2008/0208343 A1 | 8/2008 | Felt |
| 2008/0234820 A1 | 9/2008 | Felt et al. |
| 2008/0262622 A1 | 10/2008 | Butler |
| 2009/0069895 A1 | 3/2009 | Gittings et al. |
| 2009/0276047 A1 | 11/2009 | Felt et al. |
| 2010/0057144 A1 | 3/2010 | Felt et al. |
| 2010/0145457 A1 | 6/2010 | Felt et al. |

FOREIGN PATENT DOCUMENTS

| | | |
|---|---|---|
| DE | 198 23 325 | 3/2000 |
| EP | 0 353 936 | 2/1990 |
| EP | 0 378 002 | 7/1990 |
| EP | 0 505 634 | 9/1992 |
| EP | 0 521 573 | 1/1993 |
| FR | 2 639 823 | 6/1990 |
| FR | 2781998 | 2/2000 |
| WO | WO 98/20939 | 5/1988 |
| WO | WO 93/11723 | 6/1993 |
| WO | WO 95/30388 | 11/1995 |
| WO | WO 95/31946 | 11/1995 |
| WO | WO 95/31948 | 11/1995 |
| WO | WO 97/26847 | 7/1997 |
| WO | WO 99/44509 | 9/1999 |
| WO | WO99/56800 | 11/1999 |
| WO | WO 99/61084 | 12/1999 |
| WO | WO00/13619 | 3/2000 |
| WO | WO 00/59411 | 10/2000 |
| WO | WO 01/66021 | 9/2001 |
| WO | WO0217821 | 3/2002 |
| WO | WO03/099171 | 12/2003 |
| WO | WO 2004/098466 | 11/2004 |
| WO | WO2006051547 | 5/2006 |

OTHER PUBLICATIONS

U.S. Appl. No. 11/372,357, filed Dec. 28, 2006, Felt.
Toth et al., "Polyehteretherketone as a biomaterial for spinal applications," Biomaterials, 2006, pp. 324-334.
Vadapalli et al., "Biomechanical Rationale for Using Polyetheretherketone (PEEK) Spacers for Lumbar Interbody Fusion—A Finite Element Study," SPINE, 2006, vol. 31, No. 26, pp. E992-E998.
Tan et al., "Interbody Device Shape and Size are Important to Strengthen the Vertebra—Implant Interface," SPINE, 2005, vol. 30, No. 6, pp. 638-644.
Powers et al., "Minimally Invasive Fusion and Fixation Techniques," Neurosurg. Clin N Am, 2006, pp. 477-489.
Ryortho, "Here Comes ProDisc," Orhopedics This Week, vol. 2, Issue 3.
Image File Wrapper for U.S. Patent No. 7,267,690.
Image File Wrapper for U.S. Patent No. 7,591,853.
International Preliminary Report on Patentabilty for International Application No. PCT/US2007/024262 dated Jun. 4, 2009.
International Search Report for International Application No. PCT/US06/20152 dated Sep. 12, 2008.
International Search Report for International Application No. PCT/US07/24262 dated Oct. 30, 2008.
Spine-Tech, Inc., "Summary of Safety and Effectiveness," May 23, 1996, 100 pages, Minneapolis, Minnesota.
RSB Spine, LLC, "510(k) Summary," Sep. 18, 2007, 4 pages, Cleveland, Ohio.
Synthes Spine, "510 (k) Summary—Revised Sep. 2007" 5 pages, Sep. 14, 2007West Chester, Pennsylvania.
Shin et al., "Posterior Lumbar Interbody Fusion via a Unilateral Approach," Yonsei Medical Journal, 2006, vol. 47, pp. 319-325.
Vertebral Technologies, "InterFuse® Interbody Fusion System," 2009, pamphlet.
An et al., "The Future of Spinal Fuzion. Txt." ORTHO SuperSite, Aug. 2006 pp. 1-3.
Andersson et al., "Macintosh Arthroplasty in Rheumatoid Arthritis," Department of Orthopaedic Surgery and Department of Rheumatology, The London Hospital, London, England, 1974, pp. 245-259.
Cameron et al., "Review ofa Failed Knee Replacement and Some Observations on the Design of a Knee Resurfacing Prosthesis," Archives of Orthopaedic and Traumatic Surgery, vol. 97, No. 1, 1980, pp. 87-89.
Clary et al., "Experience with the MacIntosh Knee Prosthesis," Southern Medical Journal, Journal of the Southern Medical Association, Mar. 1972, vol. 65, No. 3, pp. 265-272.
Conaty, "Surgery of the Hip and Knee in Patients with Rheumatoid Arthritis," The Arthritis Servie (surgery) of Rancho, Los Amigos Hospital, Downey, Mar. 1973, vol. 55-A, No. 2, pp. 301-314.

Emerson et al., "The Use of the McKeever metallic Hemiarthroplasty for Unicompartmental Arthritis," The Journal of Bone and Joint Surgery, 1985, pp. 208-212.

Hastings, "Double Hemiarthroplasty of the Knee in Rheumatoid Arthritis," The Journal of Bone and Joint Surgery, Feb. 1973, vol. 55 B, No. 1, pp. 112-118.

Jessop et al., "Follow-up of the Macintosh Arthroplasty of the Knee Joint," Rheum. Phys. Med., 1972, vol. XI, No. 5, pp. 224.

Kay et al., "The Macintosh Tibial Plateau Hemiprosthesis for the Rheumatoid Knee," The Journal of Bone and Joint Surgery, May 1972, vol. 54B, No. 2, pp. 256-262.

Kozinn et al., "Surgical Treatment of Unicompartmental Degenerative Arthritis of the Knee," Rheumatic Disease Clinics of North America, Dec. 1988, vol. 14, No. 3, pp. 545-564.

MacIntosh et al., "The Use of the Hemiarthroplasty Prosthesis for Advanced Osteoarthritis and Rheumatoid Arthritis of the Knee," The Journal of Bone and Joint Surgery, May 1972, vol. 54 B, No. 2, pp. 244-255.

McCallum et al., "Duplication of Medial Erosion in Unicompartmental Knee Arthroplasties," The Journal of Bone and Joint Surgery, 1995, pp. 726-728.

McCollum et al., "Tibial Plateau Prosthesis in Arthroplasty of the Knee," The Journal of Bone and Joint Surgery, Jun. 1970, vol. 52-A., No. 4, pp. 827-828.

Porter, "MacIntosh Atroplasty: a long-term review," J.R. Coll. Surg. Edinb., Aug. 1988, vol. 33, pp. 199-201.

Potter, "Arthroplasty of the Knee in Rheumatoid Arthritis and Osteoarthritis," The Journal of Bone and Joint Surgery, Jan. 1972, vol. 54-A, No. 1, pp. 1-24.

Potter, "Arthroplasty of the Knee with Tibial Metallic Implants of the McKeever and MacIntosh Design," Surgical Clinics of North America, Aug. 1969, vol. 49, No. 4, pp. 903-915.

Sbarbaro, "Hemitibial plateau prosthesis ten years experience in 500 knee arthroplasties," Acta Orthopaedica Belgica, 1973, pp. 91-100.

Scott et al., "McKeever Metallic Hemiarthroplasty of the Knee in Unicompartmental Degenerative Arthritis," The Journal of Bone and Joint Surgery, Feb. 1985, vol. 67-A, No. 2, pp. 203-207.

Stauffer et al., "The MacIntosh Prosthesis, Prospective Clinical and Gait Evaluation," Arch Surg, Jun. 1975, vol. 110, pp. 717-720.

Swanson et al., "Unicompartmental and Bicompartmental Arthroplasty of the Knee with a Finned Metal Tibial-Plateau Implant," The Journal of Bone and Joint Surgery, Oct. 1985, vol. 67-A, No. 8, pp. 1175-1182.

Wayne, "Use of the McIntosh Prosthesis in Surgical Reconstruction of the Knee," Abstracts of the 1971 Proceedings, Jun. 1972, No. 85, pp. 292-293.

Wordsworth et al., "MacIntosh Arthroplasty for the rheumatoid knee: a 10-year follow up," Annals of the Rheumatic Diseases, 1985, pp. 738-741.

Chinese Office Action for Chinese Application No. 200680018453.0 dated Jan. 12, 2011. English Translation.

Japanese Office Action for Japanese Application No. 2008-513686 dated Feb. 1, 2011. (English translation).

Australian Office Action for Australian patent application No. 2010200382 dated Mar. 24, 2011.

Application and File History for U.S. Appl. No. 11/372,357, filed Mar. 9, 2006, inventor Felt, as available at www.uspto.gov.

Application and File History for U.S. Appl. No. 11/900,205, filed Sep. 10, 2007, inventor Felt, as available at www.uspto.gov.

Application and File History for U.S. Appl. No. 11/900,209, filed Sep. 9, 2007, inventor Felt, as available at www.uspto.gov.

Application and File History for U.S. Appl. No. 11/372,477, filed Mar. 9, 2006, inventor Felt, as available at www.uspto.gov.

Application and File History for U.S. Appl. No. 12/435,087, filed May 4, 2009, inventor Felt, as available at www.uspto.gov.

Application and File History for U.S. Appl. No. 12/548,225, filed Aug. 26, 2009, inventor Felt, as available at www.uspto.gov.

Application and File History for U.S. Appl. No. 11/974,185, filed Oct. 11, 2007, inventor Felt, as available at www.uspto.gov.

Application and File History for U.S. Appl. No. 10/098,601, filed Mar. 15, 2002, inventor Felt, as available at www.uspto.gov.

Transaction History for U.S. Appl. No. 10/121,455, filed Apr. 12, 2002, inventor Felt.

Application and File History for U.S. Appl. No. 10/167,963, filed Jun. 12, 2002, inventor Felt, as available at www.uspto.gov.

Application and File History for U.S. Appl. No. 10/722,019, filed Nov. 24, 2003, inventor Felt, as available at www.uspto.gov.

Application and File History for U.S. Appl. No. 11/953,203, filed Dec. 10, 2007, inventor Felt, as available at www.uspto.gov.

Application and File History for U.S. Appl. No. 12/479,402, filed Jun. 5, 2009, inventor Felt, as available at www.uspto.gov.

Notice on the First Office Action, CN200680034261.9, dated Jun. 4, 2010.

International Search Report for International Application No. PCT/US2006/000558 dated Jul. 18, 2006.

Get ADR.com Top Surgeons—Latest Orthopedic Options. Nov. 29, 2005. 2 pages http://wvvvv.getadr.com/link.htm.

Zwillich, Artificial Spinal Disc Nears Approval. WebMD Medical News. Nov. 29, 2005. 4 pages. http://wvvvv.webmd.com/content/article/88/9801.htm.

Get ADR.com Top Surgeons—Latest Orthopedic Options. Nov. 29, 2005. 2 pages http://wwvv.getadr.com/maverick.htm.

Cluett, "Discetomy-Spinal Surgery to remove herniated disc", Nov. 29, 2005. 3 pages. http://orthopedica.about.com/cs/herniateddisk/a/repturedisk 3.htm.

Get ADR.com Top Surgeons—Latest Orthopedic Options (Artificial Disc Replacement). Nov. 29, 2005. 3 pages. http://www.getadr.com.

Get ADR.com Top Surgeons—Latest Orthopedic Options (Prestige Cervical ADR). Nov. 29, 2005. 3 pages. http://wvvvv.getadr.com/prestige.htm.

Application and File History for U.S. Appl. No. 11/328,498 filed Jan. 9, 2006, inventor Sweeney et al., www.uspto.gov.

Office Action for U.S. Appl. No. 11/974,185 dated May 3, 2011.

McKeever, "Tibial Plateau Prosthesis", The Classic pp. 3-12. Jan.-Feb. 1985.

Schorn et al., "MacIntosh Arthroplasty in Rheumatoid Arthritis," Rheumatology and Rehabilitation, vol. XVII, No. 3, pp. 155-163. 1978.

* cited by examiner

MULTI-COMPOSITE DISC PROSTHESIS

RELATED APPLICATIONS

The present invention claims priority to U.S. Provisional Patent Application No. 60/700,459, entitled "SPINE POLYMER PATENT," filed Jul. 19, 2005, the disclosure of which is hereby incorporated by reference. The present application is also related to co-pending application Ser. No. 11/372,357, filed on Mar. 9, 2006 entitled, "INTERLOCKED MODULAR DISC PROSTHESIS," to U.S. Provisional Patent Application No. 60/685,332, entitled "SPINE DISC NUCLEUS II," filed May 24, 2005, and to U.S. Provisional Patent Application No. 60/660,107, entitled "MODULAR DISC PROSTHESIS," filed Mar. 9, 2005, the disclosures of all of which are hereby incorporated by reference. The present invention is also related to co-pending application Ser. No. 11/372,477, filed on Mar. 9, 2006, entitled, "RAIL-BASED MODULAR DISC NUCLEUS PROSTHESIS," the disclosure of which is hereby incorporated by reference.

FIELD OF THE INVENTION

The present invention relates generally to an implantable prosthesis for repairing damaged intervertebral discs. More particularly, the present invention relates to an artificial nucleus replacement prosthesis comprising a multi-part composite disc prosthesis that includes a first softer outer biomaterial and a second harder inner biomaterial.

BACKGROUND OF THE INVENTION

The spinal motion segment consists of a unit of spinal anatomy bounded by two vertebral bodies, including the two vertebral bodies, the interposed intervertebral disc, as well as the attached ligaments, muscles, and the facet joints. The disc consists of the end plates at the top and bottom of the vertebral bones, the soft inner core, called the nucleus and the annulus fibrosis running circumferentially around the nucleus. In normal discs, the nucleus cushions applied loads, thus protecting the other elements of the spinal motion segment. A normal disc responds to compression forces by bulging outward against the vertebral end plates and the annulus fibrosis. The annulus consists of collagen fibers and a smaller amount of elastic fibers, both of which are effective in resisting tension forces. However, the annulus on its own is not very effective in withstanding compression and shear forces.

As people age the intervertebral discs often degenerate naturally. Degeneration of the intervertebral discs may also occur in people as a result of degenerative disc disease. Degenerative disc disease of the spine is one of the most common conditions causing pain and disability in our population. When a disc degenerates, the nucleus dehydrates. When a nucleus dehydrates, its ability to act as a cushion is reduced. Because the dehydrated nucleus is no longer able to bear loads, the loads are transferred to the annulus and to the facet joints. The annulus and facet joints are not capable of withstanding their increased share of the applied compression and torsional loads, and as such, they gradually deteriorate. As the annulus and facet joints deteriorate, many other effects ensue, including the narrowing of the interspace, bony spur formation, fragmentation of the annulus, fracture and deterioration of the cartilaginous end plates, and deterioration of the cartilage of the facet joints. The annulus and facet joints lose their structural stability and subtle but pathologic motions occur between the spinal bones.

As the annulus loses stability it tends to bulge outward and may develop a tear allowing nucleus material to extrude. Breakdown products of the disc, including macroscopic debris, microscopic particles, and noxious biochemical substances build up. These breakdown products stimulate sensitive nerve endings in and around the disc, producing low back pain and sometimes, sciatica. Affected individuals experience muscle spasms, reduced flexibility of the low back, and pain when ordinary movements of the trunk are attempted.

Degeneration of a disc is irreversible. In some cases, the body will eventually stiffen the joints of the motion segment, effectively re-stabilizing the discs. Even in the cases where re-stabilization occurs, the process can take many years and patients often continue to experience disabling pain. Extended painful episodes of longer than three months often leads patients to seek a surgical solution for their pain.

Several methods have been devised to attempt to stabilize the spinal motion segment. Some of these methods include: heating the annular region to destroy nerve endings and strengthen the annulus; applying rigid or semi-rigid support members on the sides of the motion segment or within the disc space; removing and replacing the entire disc with a generally rigid plastic, articulating artificial device; removing and replacing the nucleus; and spinal fusion involving permanently fusing the vertebrae adjacent the affected disc.

Until recently, spinal fusion has generally been regarded as the most effective surgical treatment to alleviate back pain due to degeneration of a disc. While this treatment is often effective at relieving back pain, all discal motion is lost in the fused spinal motion segment. The loss of motion in the affected spinal segment necessarily limits the overall spinal mobility of the patient. Ultimately, the spinal fusion places greater stress on the discs adjacent the fused segment as these segments attempt to compensate for lack of motion in the fused segment, often leading to early degeneration of these adjacent spinal segments.

Current developments are focusing on treatments that can preserve some or all of the motion of the affected spinal segment. One of these methods to stabilize the spinal motion segment without the disadvantages of spinal fusion is total disc replacement. Total disc replacement is a highly invasive and technically demanding procedure which accesses the disc from an anterior or frontal approach and includes dividing the anterior longitudinal ligament, removing the cartilaginous end plates between the vertebral bone and the disc, large portions of the outer annulus and the complete inner nucleus. Then an artificial total disc prosthesis is carefully placed in the evacuated disc space. Many of the artificial total disc prosthesis currently available consist of a generally rigid plastic such as ultra high molecular weight polyethelyene ("UHMWPE) as the nucleus that is interposed between two metal plates that are anchored or attached to the vertebral endplates. A summary of the history of early development and designs of artificial discs is set forth in Ray, "The Artificial Disc: Introduction, History and Socioeconomics," Chpt. 21, *Clinical Efficacy and Outcome in the Diagnosis of Low Back Pain*, pgs. 205-225, Raven Press (1992). Examples of these layered total disc replacement devices are shown, for example, in U.S. Pat. Nos. 4,911,718, 5,458,643, 5,545,229 and 6,533,818.

These types of artificial total discs have several disadvantages. First, because the artificial disc prostheses are relatively large, they require relatively large surgical exposures to accommodate their insertion. The larger the surgical exposure, the higher the chance of infection, hemorrhage or even morbidity. Also, in order to implant the prosthesis, a large portion of the annulus must be removed. Removing a large portion of the annulus reduces the stability of the motion segment, at least until healing occurs around the artificial disc. Further, because the devices are constructed from rigid materials, they can cause serious damage if they were to displace from the disc space and contact local nerve or vascular tissues. Another disadvantage is that rigid artificial disc replacements do not reproduce natural disc mechanics.

An alternative to total disc replacement is nucleus replacement. Like an artificial disc prosthesis, these nucleus replacements are also inert, non-biological prostheses. The procedure for implanting a nucleus replacement is less invasive than the procedure for a total disc replacement and generally includes the removal of only the nucleus and replacement of the nucleus with a prosthesis that may be malleable and provide cushioning that mimics a natural disc nucleus. Examples of the prostheses used for nucleus replacement include: U.S. Pat. Nos. 4,772,287, 4,904,260, 5,192,326, 5,919,236 and 6,726,721.

Nucleus replacements are intended to more closely mimic natural disc mechanics. To that end, some nucleus replacements utilize hydrogels because of their water imbibing properties that enable these replacements to expand in situ to permit a more complete filling of the evacuated nucleus cavity. However, there is usually a trade-off in that the more expansion the hydrogel achieves, the less structural support the end product can provide. As a result, many hydrogel nucleus disc replacements have generally adopted the use of some form of a jacket or fabric to constrain the hydrogel material. For example, the implant described in U.S. Pat. Nos. 4,772,287 and 4,904,260 consists of a block of hydrogel encased in a plastic fabric casing. The implant described in U.S. Pat. No. 5,192,326 consists of hydrogel beads enclosed by a fabric shell. Without the jacket or other form of constraint, the hydrogel is susceptible to displacement because of the slippery nature of the hydrogel. Unfortunately, the jacket or fabric shell will be subject to long term abrasive wear issues that could result in failure of jacket or shell's ability to constrain the hydrogel and thus the hydrogel may be subject to displacement.

Another approach to nucleus replacement involves implantation of a balloon or other container into the nucleus, which is then filled with a biocompatible material that hardens in situ. Examples of this in situ approach to nucleus replacement include U.S. Pat. Nos. 6,443,988 and 7,001,431. One of the problems with this approach is that the chemical hardening process is exothermic and can generate significant amounts of heat that may cause tissue damage. In addition, there is a possibility that the balloon may rupture during expansion, causing leakage of material into the disc cavity and surrounding tissues, which may cause undesirable complications.

Yet another approach is disclosed in U.S. Pat. No. 5,865,846 to Bryan et al. in which a softer inner material is contained within a harder outer shell. The Bryan patent discloses the use of a resilient body made of two or more biocompatible materials wherein the soft inner portion of the body has a Shore D hardness of 30 and the harder outer portion has a Shore D hardness of 90. A similar approach using elastomers is described in U.S. Patent Publ. Appl. No. 2005/0119752A1 to Williams et al that discloses an artificial intervertebral disc fabricated of hydrogel, polyurethane, thermoplastic elastomers or other biocompatible materials wherein the softer inner nucleus portion has a Shore A hardness in the range of 20-70 and the harder outer portion has a Shore A hardness in the range of 35-90. While seemingly similar to the natural soft-hard combination of the disc nucleus and annulus, these implants still have the same approach and problems as the sandwiched metal and polymer implants.

Accordingly, there is a need for a nucleus disc replacement that addresses the shortcomings of the current approaches.

SUMMARY OF THE INVENTION

The present invention is a multi-composite disc prosthesis that is adapted to be implanted within the annulus of an evacuated disc nucleus space in a human spine. The disc prosthesis has a generally solid unitary body with a size and a shape adapted to be positioned within the annulus of the evacuated disc nucleus space. The body has an outer portion comprised of a first biomaterial and an inner portion comprised of a second biomaterial. The second biomaterial has a compressive modulus that is harder than the compressive modulus of the first biomaterial and the first and second biomaterials may be bonded together to form a multi-composite material that forms the solid body.

The present invention is an alternative to total disc replacement. The device of the present invention uses biocompatible materials to replace the disc nucleus. The present invention has many advantages over currently available nucleus replacements. One such advantage is that in certain embodiments the nucleus replacement of the present invention may be inserted through a minimally invasive procedure through a small hole in the posterior annulus, leaving much of the annulus and surrounding vertebral cartilage intact.

Further, the device of the present invention will offer pain relief by retensioning the annulus, providing a cushioning effect and restoring a more normal distribution of pressure between the annulus and the nucleus. In one embodiment of the device of the present invention, the nucleus replacement consists of at least two biocompatible materials including an inner layer of a hard modulus biomaterial and an outer surrounding coat of a softer modulus biomaterial.

In one aspect of the present invention, the implant may include an outer soft modulus biomaterial and inner hard modulus biomaterial. In another aspect of the present invention, the outer soft modulus biomaterial and the inner hard modulus biomaterial may be chemically bonded.

In another aspect of the present invention the implant comprises a composite system of two biomaterials, wherein the biomaterials may consist of a biocompatible polyurethane based on a diisocyanate and a polyol.

In one aspect of the invention, the implant may consist of several interconnected segments that slide along a track formed of the hard modulus material such that each segment is sequentially inserted into the disc space and connected to the other segments forming a unitary device.

DETAILED DESCRIPTION OF THE EMBODIMENTS

In contrast to conventional disc or nucleus replacements, the present invention comprises a composite system wherein the outer portion consists of soft modulus material mimicking the natural disc and the inner portion consists of harder modulus material which provides support and stability. Two biocompatible polymers may be chemically bonded to form the composite system of the present invention. Many conventional total disc replacements include upper and lower rigid plates and a non-rigid material disposed therebetween, while other existing nuclear replacements consist of a mass of soft material without a stabilizing hard inner core. The composite system of the present invention offers advantages over the existing devices in that the soft outer portion provides cushioning while not eroding the endplates as may happen with harder materials of other disc nucleus replacements. Further, the soft outer portion is deformable to correspond to the desired modulus in response to normal physiologic forces of about 30 to 300 pounds. Because of this deformability, the prosthesis produces a physiologically appropriate amount of loading on the end plates of the intervertebral disc. As a result, the end plates will not excessively deform over time and ultimately conform to the contours of the implant as is the case with more rigid disc nucleus replacement implants. Further, the harder inner core of the present invention provides support and stability lacking in the implants made of hydrogel blocks or chunks.

Figure 1:
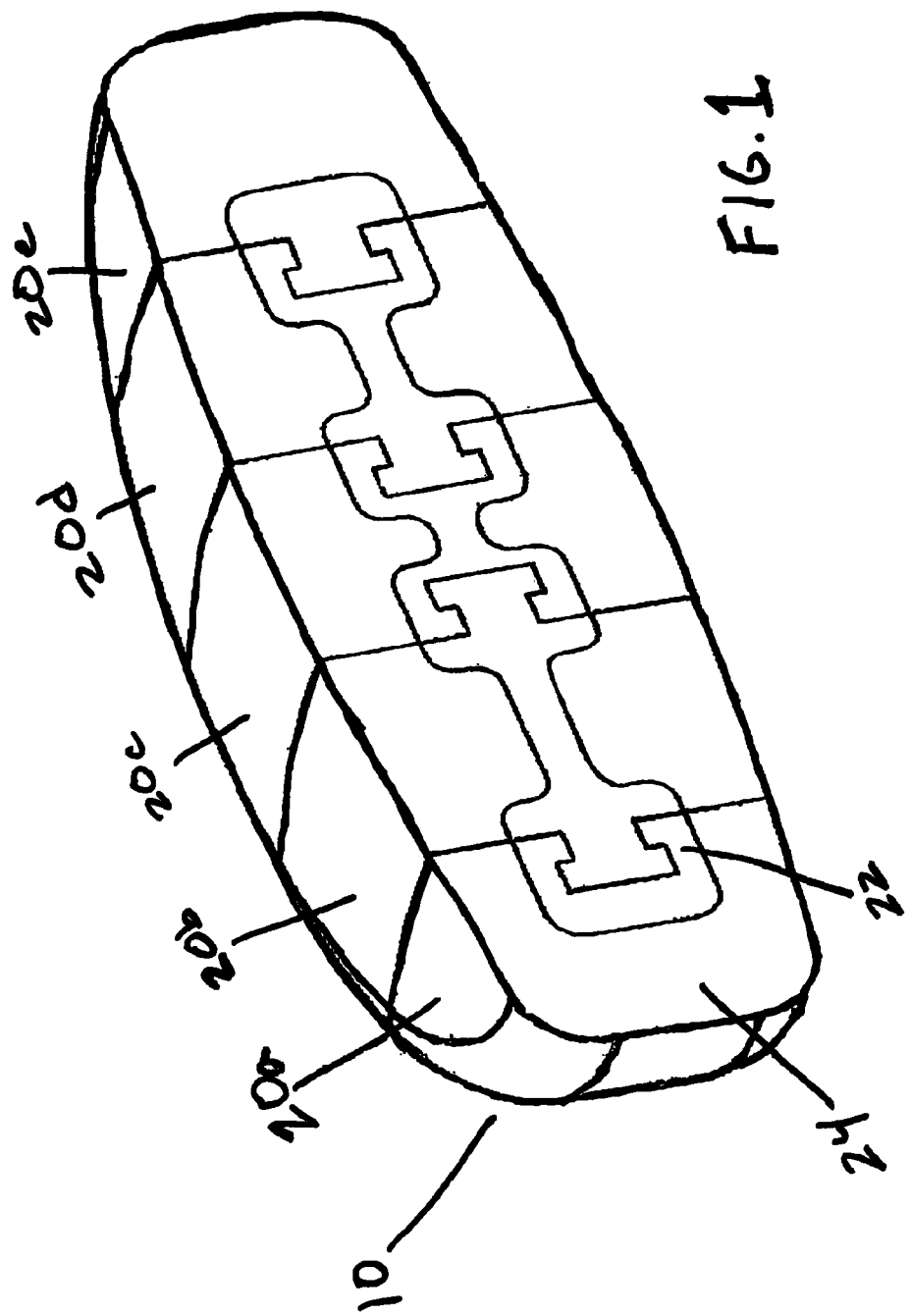
FIG. 1 is a cross sectional view of a modular disc prosthesis according to the present invention.

In an embodiment of the present invention, the nucleus replacement 10 may include several components that are sequentially inserted into the evacuated disc nucleus space. This sequential insertion allows for a small surgical exposure because the device is inserted one component at a time as opposed to some problematic devices that are inserted in their entirety requiring a larger surgical exposure. As shown in FIG. 1, each component 20 may be composed of an inner connecting track of hard modulus biomaterial 22 and an outer surrounding coat of a softer modulus biomaterial 24. During insertion, the first component may slide along a track consisting of a high modulus biomaterial and into place within the disc annulus. In one embodiment, the device is inserted in a minimally invasive procedure through a small opening in the posterior annulus. Each component may mechanically interlock with the adjacent component such that when all components are fully inserted, the interlocked components comprise a single unit.

In one embodiment, the device of the present invention may consist of two biocompatible materials of different hardness. In an embodiment of the device, the biomaterials may consist of a biocompatible polyurethane based on a diisocyanate and a polyol. In one embodiment, the isocyanate component may be 4,4'-diphenylmethane diisocyanate ('MDI') and the polyol component may be a combination of polytetramethyleneoxide ("PTMO") 1000 and PTMO 2000. The polymers may also contain a chain extender, a cross linking agent and a catalyst. In one embodiment, the chain extender may be 1,4-butanediol ("BDO"); the cross linking agent may be trimethylpropane ("TMP") and the catalyst may be bis-(dodecylthio)-dimethylstannane ("Fomrez catalyst UL22"). The two biomaterials may be bonded together forming a composite system. For example, such bonding may be chemical or physical. In one aspect of the present invention, such bonding may include a urethane bond.

One of ordinary skill in the art will recognize that additional biomaterials and constituents of the biomaterials suitable for the composition of the present nucleus prosthesis are contemplated and are within the scope of the present disclosure. Other biomaterials that may be used within the scope of the present invention include, but are not limited to: hydrogels, rubbers, silicones, thermoplastic elastomers, acrylate monomers, curable epoxies, curable monomers and any combination thereof.

In one embodiment of the device, the outer surrounding coat of the device may be comprised of a first biomaterial consisting of a softer polymer that provides cushioning and support, mimicking the characteristics of a natural disc nucleus. In an embodiment of the device, the outer polymer may be modified to provide for elution of medicants such as analgesics, antibiotics, antineoplastics, or biosteologics such as bone growth agents or any other desired material. While motion preservation is generally a principle goal in nucleus replacement, in certain indications it may be desirable to promote some bony fusion. Such indications may include nuclear replacements in the cervical spine.

The solid polymer outer shell of the modular disc nucleus prosthesis may provide for better and more controllable elution rates than some hydrogel materials. In an alternate embodiment, the modular disc nucleus prosthesis may include different elution rates for each polymer material. This would allow for varying elution rates for different medicants.

The softer biomaterial may consist of a harder segment content in the range of about 15 to 25 weight percent. One of ordinary skill in the art will recognize that additional ranges of hard segment weight percent within this explicit range are contemplated and are within the scope of the present disclosure. The softer biomaterial may have a compressive modulus in the range of about 10-20 MPa. For example, the softer biomaterial may have a Shore A hardness no greater than 80 and a Shore D hardness no greater than 40. The tensile strength of the softer biomaterial may be in the range of 10-30 MPa. In an embodiment of the present device, the softer biomaterial may have a yield strength of 1-1.5 MPa. The modulus of elasticity of the softer biomaterial may be in the range of 6-8 MPa. One of ordinary skill in the art will recognize that additional ranges within the explicit ranges set forth hereinabove are contemplated and are within the scope of the present disclosure.

One embodiment of device may further include a second biomaterial. The second biomaterial may consist of a harder polymer of high durometer, preferably of at least a Shore D hardness of 55. The hardness of the second biomaterial provides structural support for the insertion track and the interlocking mechanism. In an alternative embodiment, the first or second biomaterial may consist of a thermoplastic polyetherurethane or polycarbonate-urethane, such as Pellethane®, Tecothane® or Bionate®. In an embodiment, the first or second biomaterial may consist of poly-ether-ether-ketone (PEEK) or another polymer of similar stiffness. In another alternative embodiment, the second biomaterial may consist of a MDI, PTMO based polyurethane processed to have a hard segment weight content in the range of about 50 to 70 percent, smaller homogenous molecular weight chain lengths in the prepolymer and an optimal micro-phase separation of the hard and soft segment components to provide a macroscopically homogenous distribution in the cured polymer. One of ordinary skill in the art will recognize that additional ranges of hard segment weight percent within this explicit range are contemplated and are within the scope of the present disclosure.

The harder biomaterial may have a tensile strength in the range of 40-75 MPa. The yield strength of the harder biomaterial may be in the range of 20-45 MPa. The harder biomaterial may have a modulus of elasticity in the range of 400-700 MPa. The compressive modulus of the harder biomaterial may be in the range of 200-400 MPa. One of ordinary skill in the art will recognize that additional ranges within the explicit ranges set forth hereinabove are contemplated and are within the scope of the present disclosure.

In an aspect of the first softer biomaterial, the weight percent of the MDI may be in a range of 5 to 35 weight percent of the total cured polymer. In an alternate embodiment of the first softer biomaterial, the weight percent of the MDI may be in a range of 15 to 25 weight percent of the total cured polymer. In one embodiment, the weight percent of the MDI may be in a range of about 18 to 20 weight percent of the total cured polymer. One of ordinary skill in the art will recognize that additional ranges of MDI weight percent of the total cured polymer within the above described explicit ranges are contemplated and are within the scope of the present disclosure.

The weight percent of the PTMO 1000 of the first softer biomaterial may be in a range of 0 to 40 weight percent of the total cured polymer. In an alternate embodiment, the weight percent of the PTMO 1000 may be in a range of 10 to 30 weight percent of the total cured polymer. In one embodiment, the weight percent of the PTMO 1000 may be in a range of 25 to 27 weight percent of the total cured polymer. One of ordinary skill in the art will recognize that additional ranges of PTMO 1000 weight percent of the total cured polymer within the above described explicit ranges are contemplated and are within the scope of the present disclosure.

The weight percent of the PTMO 2000 of the first softer biomaterial may be in a range of 0 to 80 weight percent of the total cured polymer. In an alternate embodiment, the weight percent of the PTMO 2000 may be in a range of 40 to 60 weight percent of the total cured polymer. In one embodiment, the weight percent of the PTMO 2000 may be in a range of 52 to 54 weight percent of the total cured polymer. One of ordinary skill in the art will recognize that additional ranges of PTMO 2000 weight percent of the total cured polymer within the above described explicit ranges are contemplated and are within the scope of the present disclosure.

The weight percent of the BDO of the first softer biomaterial may be in a range of 0 to 10 weight percent of the total cured polymer. In an alternate embodiment, the weight percent of the BDO may be in a range of 0 to 5 weight percent of the total cured polymer. In one embodiment, the weight percent of the BDO may be in a range of 1 to 2 weight percent of the total cured polymer. One of ordinary skill in the art will recognize that additional ranges of BDO weight percent of the total cured polymer within the above described explicit ranges are contemplated and are within the scope of the present disclosure.

The weight percent of the TMP of the first softer biomaterial may be in a range of 0 to 5 weight percent of the total cured polymer. In an alternate embodiment, the weight percent of the TMP may be in a range of 0 to 0.1 weight percent of the total cured polymer. In one embodiment, the weight percent of the TMP may be in a range of 0.06 to 0.08 weight percent of the total cured polymer. One of ordinary skill in the art will recognize that additional ranges of TMP weight percent of the total cured polymer within the above described explicit ranges are contemplated and are within the scope of the present disclosure.

The weight percent of the UL22 of the first softer biomaterial may be in a range of 0 to 2 weight percent of the total cured polymer. In an alternate embodiment, the weight percent of the UL22 may be in a range of 0 to 1 weight percent of the total cured polymer. In one embodiment, the weight percent of the UL22 may be in a range of 0.0001 to 0.0030 weight percent of the total cured polymer. One of ordinary skill in the art will recognize that additional ranges of UL22 weight percent of the total cured polymer within the above described explicit ranges are contemplated and are within the scope of the present disclosure.

In one aspect of the first softer biomaterial, the combined weights of the MDI and BDO generally correlate to the hard segment content and hardness of the cured polymer. In an embodiment of the first softer biomaterial, the combined weight percentage of the MDI and BDO may be in a range of about 15 to 25 weight percent of the total cured polymer. In one embodiment of the first softer biomaterial, the combined weight percentage of the MDI and BDO may be in a range of about 20 to 22 weight percent of the total cured polymer. One of ordinary skill in the art will recognize that additional ranges of combined MDI and BDO weight percentages of the total cured polymer within the above described explicit ranges are contemplated and are within the scope of the present disclosure.

The first softer biomaterial may comprise two separate prepolymers, Part A and Part B, that are mixed together to form the cured polymer. In one embodiment, Part A is formed by processing MDI and PTMO 2000 together and Part B is formed by processing PTMO 1000, BDO, TMP and UL22 together. Any combination of MDI, PTMO 1000, PTMO 2000, BDO, TMP, UL22 and/or other suitable constituents may be processed to form the prepolymers, Part A and Part B. In an embodiment of the first softer biomaterial where Part A and Part B are mixed together to form the cured polymer, Part A and Part B may be mixed such that the total isocyanate to polyol ratio is in the range of about 0.96 to 1.04. In one embodiment, Part A and Part B may be mixed together such that the total isocyanate to polyol ratio is in the range of about 1.01 to 1.03. One of ordinary skill in the art will recognize that additional ranges of total isocyantate to polyol ratios within the above described explicit ranges are contemplated and are within the scope of the present disclosure.

The weight percent of the MDI of the second harder biomaterial may be in a range of 30 to 70 weight percent of the total cured polymer. In an alternate embodiment of the second harder biomaterial, the weight percent of the MDI may be in a range of 40 to 60 weight percent of the total cured polymer. In one embodiment of the second harder biomaterial, the weight percent of the MDI may be in a range of about 47 to 49 weight percent of the total cured polymer. One of ordinary skill in the art will recognize that additional ranges of MDI weight percent of the total cured polymer within the above described explicit ranges are contemplated and are within the scope of the present disclosure.

The weight percent of the PTMO 1000 of the second harder biomaterial may be in a range of 0 to 40 weight percent of the total cured polymer. In an alternate embodiment of the second harder biomaterial, the weight percent of the PTMO 1000 may be in a range of 10 to 30 weight percent of the total cured polymer. In one embodiment of the second harder biomaterial, the weight percent of the PTMO 1000 may be in a range of about 20 to 22 weight percent of the total cured polymer. One of ordinary skill in the art will recognize that additional ranges of PTMO 1000 weight percent of the total cured polymer within the above described explicit ranges are contemplated and are within the scope of the present disclosure.

The weight percent of the PTMO 2000 of the second harder biomaterial may be in a range of 0 to 40 weight percent of the total cured polymer. In an alternate embodiment of the second harder biomaterial, the weight percent of the PTMO 2000 may be in a range of 10 to 30 weight percent of the total cured polymer. In one embodiment of the second harder biomaterial, the weight percent of the PTMO 2000 may be in a range of about 15 to 17 weight percent of the total cured polymer. One of ordinary skill in the art will recognize that additional ranges of PTMO 2000 weight percent of the total cured polymer within the above described explicit ranges are contemplated and are within the scope of the present disclosure.

The weight percent of the BDO of the second harder biomaterial may be in a range of 0 to 35 weight percent of the total cured polymer. In an alternate embodiment of the second harder biomaterial, the weight percent of the BDO may be in a range of 5 to 25 weight percent of the total cured polymer. In one embodiment of the second harder biomaterial, the weight percent of the BDO may be in a range of about 14 to 16 weight percent of the total cured polyurethane. One of ordinary skill in the art will recognize that additional ranges of BDO weight percent of the total cured polymer within the above described explicit ranges are contemplated and are within the scope of the present disclosure.

The weight percent of the TMP of the second harder biomaterial may be in a range of 0 to 5 weight percent of the total cured polyurethane. In an alternate embodiment of the second harder biomaterial, the weight percent of the TMP may be in a range of 0 to 1 weight percent of the total cured polyurethane. In one embodiment of the second harder biomaterial, the weight percent of the TMP may be in a range of about 0.1 to 0.3 weight percent of the total cured polyurethane. One of ordinary skill in the art will recognize that additional ranges of TMP weight percent of the total cured polymer within the above described explicit ranges are contemplated and are within the scope of the present disclosure.

The weight percent of the UL22 of the second harder biomaterial may be in a range of 0 to 2 weight percent of the total cured polyurethane. In an alternate embodiment of the second harder biomaterial, the weight percent of the UL22 may be in a range of 0 to 1 weight percent of the total cured polyurethane. In one embodiment of the second harder biomaterial, the weight percent of the UL22 may be in a range of about 0.0001 to 0.002 weight percent of the total cured polyurethane. One of ordinary skill in the art will recognize that additional ranges of UL22 weight percent of the total cured polymer within the above described explicit ranges are contemplated and are within the scope of the present disclosure.

In one embodiment of the second harder biomaterial, the combined weights of the MDI and the BDO generally correlate to the hard segment content and hardness of the cured polymer. The combined weight of the MDI and BDO may be in the range of about 50 to 70 weight percent of the total weight of the cured polymer. In one embodiment, the combined weight of the MDI and BDO may be in the range of about 62 to 64 weight percent of the total weight of the cured polymer. One of ordinary skill in the art will recognize that additional ranges of combined MDI and BDO weight percent of the total cured polymer within the above described explicit ranges are contemplated and are within the scope of the present disclosure.

Figure 2:
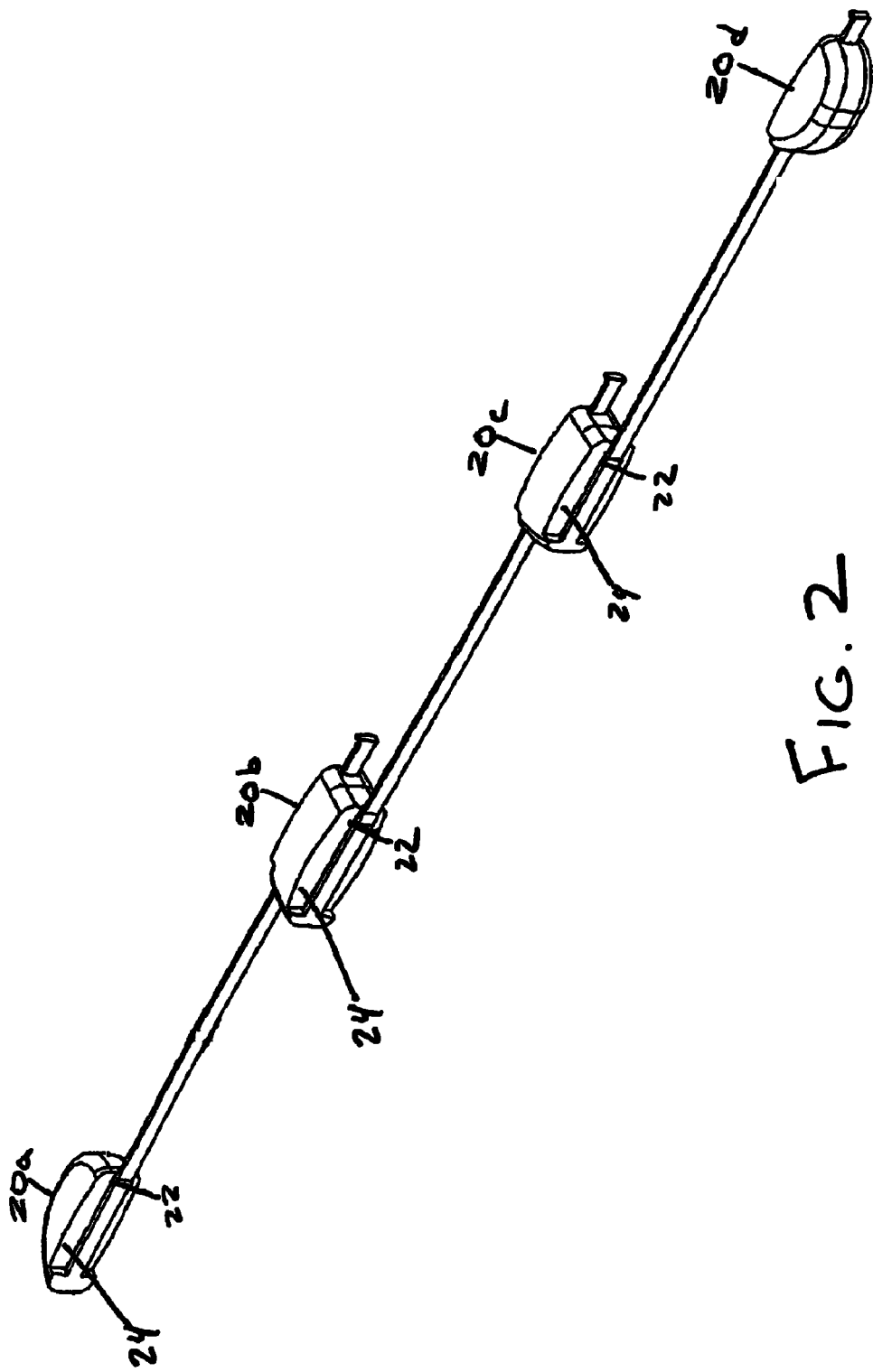
FIG. 2 is a view of a modular disc prosthesis according to the present invention at a first stage of insertion.
Figure 3:
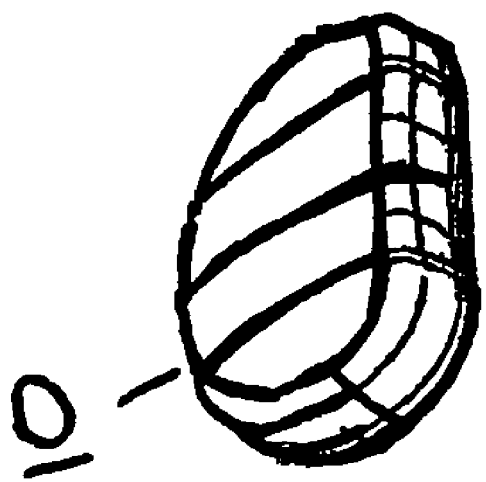
FIG. 3 is a view of a modular disc prosthesis according to the present invention at the final stage of insertion.

For a more detailed description of one tracked embodiment of FIGS. 2 and 3 of the present invention, reference is made to the previously identified co-pending application entitled, "RAIL-BASED MODULAR DISC PROTHESIS," the disclosure of which is hereby incorporated by reference.

In one aspect of the implant of the present invention, the second harder biomaterial may be comprised of two separate prepolymers, Part A and Part B. Part A and Part B may be selected from the group consisting of MDI, TDI, PTMO 1000, PTMO 2000, BDO, TMP, UL22 or any other combination of suitable constituents. Further, Part A may be processed such that the prepolymer contains smaller molecular weight chain lengths of one or two polymer populations than that of Part B. In one embodiment, the MDI, PTMO 1000 and PTMO 2000 are processed together to form the Part A. Preferably, the BDO, TMP and UL22 are processed together to form the Part B. Part A and Part B may be mixed such that the total isocyanate to polyol ratio is in the range of about 0.96 to 1.04. In one embodiment, the isocyanate to polyol ratio is in the range 1.01 to 1.03. One of ordinary skill in the art will recognize that additional ranges of isocyanate to polyol ratios within the above described explicit ranges are contemplated and are within the scope of the present disclosure. Various modifications to the disclosed apparatuses and methods may be apparent to one of skill in the art upon reading this disclosure. The above is not contemplated to limit the scope of the present invention, which is limited only by the claims below.

The invention claimed is:

1. A disc prosthesis that is adapted to be implanted within the annulus of an evacuated disc nucleus space in a human spine, the evacuated disc nucleus space being defined at least in part by tissue superior to the evacuated disc nucleus space and tissue inferior to the evacuated disc nucleus space, the disc prosthesis comprising, a generally solid unitary body having a size and a shape adapted to be positioned within the annulus of the evacuated disc nucleus space, wherein the solid unitary body is comprised of a plurality of interconnected segments that are positioned situ within the evacuated disc space to form the size and the shape of the solid unitary body, the body having: an outermost portion comprised of a first biomaterial and presenting a surface adapted to contact at least one of the tissue superior to the evacuated disc nucleus space and the tissue inferior to the evacuated disc nucleus space; and an innermost portion defining an inner core that provides support and stability for the solid body, the inner core comprised of a second biomaterial, wherein the outermost portion surrounds the innermost portion in an assembled configuration in situ, the inner core being of a compressive modulus that is harder than a compressive modulus of the outermost portion, first biomaterial and wherein the first and second biomaterials together form a multi-composite material comprising the solid body, and wherein the first biomaterial and the second biomaterial are bonded together at an interface such that the outermost portions and the innermost portion are held in a fixed spatial relationship with respect to each other at said interface.

2. The disc prosthesis of claim 1 wherein the first biomaterial and the second biomaterial are chemically bonded.

3. The disc prosthesis of claim 1 wherein the first biomaterial and the second biomaterial are physically bonded.

4. The disc prosthesis of claim 1 wherein the first biomaterial and the second biomaterial are each polymers.

5. The disc prosthesis of claim 4 wherein the first biomaterial and the second biomaterial are each a polyurethane.

6. The disc prosthesis of claim 5 wherein the polyurethane is comprised of a diisocyanate and a polyol.

7. The disc prosthesis of claim 5 wherein the components of the polyurethane are selected from the group consisting of: diisocyanates, polyols, catalysts, chain extenders and cross-linking agents.

8. The disc prosthesis of claim 5, wherein the polyurethane of the first biomaterial has a hard segment content in the range of about 15 to 25 weight percent.

9. The disc prosthesis of claim 5, wherein the polyurethane of the second biomaterial has a hard segment content in the range of about 50 to 70 weight percent.

10. The disc prosthesis of claim 4 wherein the second biomaterial is selected from the group consisting of: a thermoplastic polyether-urethane, polycarbonate-urethane and poly-ether-ether-ketone.

11. The disc prosthesis of claim 4, wherein the first biomaterial is selected from the group consisting of: a thermoplastic polyether-urethane and polycarbonate-urethane.

12. The disc prosthesis of claim 1, wherein the compressive modulus of the first biomaterial is in the range of about 10-20 MPa.

13. The disc prosthesis of claim 1, wherein the second biomaterial has a Shore D hardness of at least 55.

14. The disc prosthesis of claim 1, wherein at least an outermost layer of the outer portion further comprises at least one medicant operably carried by the first biomaterial to be eluted after the prosthesis is implanted.

15. The disc prosthesis of claim 1, wherein the compressive modulus of the second biomaterial is at least 200 Mpa.

16. A disc prosthesis that is adapted to be implanted within the annulus of an evacuated disc nucleus space in a human spine, the evacuated disc nucleus space being defined at least in part by tissue superior to the evacuated disc nucleus space and tissue inferior to the evacuated disc nucleus space, the disc prosthesis comprising, a generally solid unitary body having a size and shape adapted to be positioned within the annulus of the evacuated disc nucleus space, wherein the solid unitary body is comprised of a plurality of interconnected segments that are positioned in situ within the evacuated disc space to form the size and the shape of the unitary body, the body having: an outermost portion comprised of a first biomaterial and presenting a surface adapted to contact at least one of the tissue superior to the evacuated disc nucleus space and the tissue inferior to the evacuated disc nucleus space; and an innermost portion defining an inner core comprised of a second biomaterial and arranged as a structure that provides support and stability for the solid body, wherein the outermost portion surrounds the innermost portion in an assembled configuration in situ, the second biomaterial has a compressive modulus greater than 200 Mpa that is harder than a compressive modulus of the first biomaterial by at least an order of magnitude and the first and second biomaterials together form a multi-composite material comprising the solid body, and wherein the first biomaterial and the second biomaterial are bonded together at an interface such that the outermost portion and the innermost portion are held in a fixed spatial relationship with respect to each other at said interface.

17. The disc prosthesis of claim 16 wherein the first biomaterial and the second biomaterial are chemically bonded.

18. The disc prosthesis of claim 16 wherein the first biomaterial and the second biomaterial are physically bonded.

19. The disc prosthesis of claim 16 wherein the first biomaterial and the second biomaterial are each polymers.

20. The disc prosthesis of claim 19 wherein the first biomaterial and the second biomaterial are each polyurethane.

21. The disc prosthesis of claim 20 wherein the polyurethane is comprised of a diisocyanate and a polyol.

22. The prosthesis of claim 20 wherein the components of the polyurethane are selected from the group consisting of: diisocyanates, polyols, catalysts, chain extenders and cross-linking agents.

23. The disc prosthesis of claim 20 wherein the polyurethane of the first biomaterial has a hard segment content in the range of about 15 to 25 weight percent.

24. The disc prosthesis of claim 20 wherein the polyurethane of the second biomaterial has a hard segment content in the range of about 50 to 70 weight percent.

25. The disc prosthesis of claim 19 wherein the second biomaterial is selected from the group consisting of: a thermoplastic polyether-urethane, polycarbonate-urethane and poly-ether-ether-keytone.

26. The disc prosthesis of claim 19 wherein the first biomaterial is selected from the group consisting of: a thermoplastic polyether-urethane and polycarbonate-urethane.

27. The disc prosthesis of claim 16 wherein the compressive modulus of the first biomaterial is in the range of about 10-20 Mpa.

28. The disc prosthesis of claim 16 wherein the second biomaterial has a Shore D hardness of at least 55.

29. The disc prosthesis of claim 16 wherein at least an outermost layer of the outer portion further comprises at least one medicant operably carried by first biomaterial to be eluted after the prosthesis is implanted.

* * * * *